United States Patent
Zucherman et al.

(10) Patent No.: US 8,172,852 B2
(45) Date of Patent: May 8, 2012

(54) SYSTEMS AND METHODS FOR INJECTING BONE FILLER INTO THE SPINE

(75) Inventors: James F. Zucherman, San Francisco, CA (US); Ken Y. Hsu, San Francisco, CA (US)

(73) Assignee: Spartek Medical, Inc., Concord, CA (US)

( * ) Notice: Subject to any disclaimer, the term of this patent is extended or adjusted under 35 U.S.C. 154(b) by 821 days.

(21) Appl. No.: 12/236,959

(22) Filed: Sep. 24, 2008

(65) Prior Publication Data

US 2009/0093817 A1    Apr. 9, 2009

Related U.S. Application Data

(60) Provisional application No. 60/997,973, filed on Oct. 5, 2007.

(51) Int. Cl.
*A61B 17/58* (2006.01)
*A61B 17/60* (2006.01)
*A61F 2/00* (2006.01)

(52) U.S. Cl. ..... 606/94; 606/248; 623/17.11; 623/17.12

(58) Field of Classification Search ............... 606/92–94, 606/248; 623/17.12, 17.11
See application file for complete search history.

(56) References Cited

U.S. PATENT DOCUMENTS

| | | | |
|---|---|---|---|
| 6,048,346 A | 4/2000 | Reiley et al. | |
| 6,676,664 B1 | 1/2004 | Al-Assir | |
| 6,773,437 B2 | 8/2004 | Ogilvie et al. | |
| 7,611,526 B2 * | 11/2009 | Carl et al. | 606/248 |
| 7,722,624 B2 * | 5/2010 | Boucher et al. | 606/105 |
| 7,931,689 B2 * | 4/2011 | Hochschuler et al. | 623/17.12 |
| 2008/0027434 A1 | 1/2008 | Zucherman et al. | |
| 2008/0027435 A1 | 1/2008 | Zucherman et al. | |

* cited by examiner

*Primary Examiner* — Andrew Yang
(74) *Attorney, Agent, or Firm* — Fliesler Meyer LLP

(57) ABSTRACT

Systems and methods for injecting bone filler into a vertebra, wherein a spinous process and/or lamina can be strengthened by injecting the bone filler into the spinous process and/or lamina. An insertion device including a needle can be positioned proximal to the junction between the spinous process and the lamina of the vertebra when inserting the bone filler. Various embodiments of the needle and needle guide devices can be used to facilitate the process.

16 Claims, 14 Drawing Sheets

SYSTEMS AND METHODS FOR INJECTING BONE FILLER INTO THE SPINE

CLAIM OF PRIORITY

This application claims priority to U.S. Provisional Application No. 60/977,973, filed Oct. 5, 2007, entitled "Systems and Methods for Injecting Bone Filler into the Spine", which is incorporated herein by reference in its entirety.

FIELD OF THE INVENTION

This present invention relates generally to spinal surgery, particularly systems and methods for injecting bone filler into the spine.

BACKGROUND

The human vertebral column (or "spine") connects the skull to the pelvis and includes a column of vertebrae, the sacrum, intervertebral discs and the coccyx. The vertebrae, which are the bones of the spine, function to bear the weight of the body and to house the spinal cord and spinal nerve roots within the vertebral column. There are two major parts to each vertebra: (1) the anterior (front) segment, which is the vertebral body; and (2) a posterior part (the vertebral arch) which encloses the vertebral foramen. The vertebral arch includes a pair of pedicles, a pair of laminae, and seven processes, four articular, two transverse and one spinous. The transverse processes are relatively long and slender while the spinous processes are relatively broad and thick. The processes provide sites for the attachment of ligaments and muscles which are important for the stability and movement of the spine.

Intervertebral discs lie between adjacent vertebrae in the spine. Each intervertebral disc includes a soft jelly-like center called the nucleus pulposus, which is surrounded by the annulus fibrosis, which includes several layers of fibrocartilage. The nucleus pulposus acts as a shock absorber for the spine, absorbing the impact of the body's daily activities and keeping the adjacent vertebrae separated. The nucleus pulposus is predominately made of water, which gives the intervertebral disc its elastic quality. However, as people age, the nucleus pulposus begins to dehydrate, which limits its ability to absorb shock and separate the adjacent vertebrae. This disc degeneration can result in spinal stenosis, a medical condition in which the spinal canal narrows, thereby producing pressure on the nerve roots resulting in pain and discomfort. Spinal stenosis can also be caused by spinal disc herniation, osteoporosis, or a tumor. Not surprisingly, many different types of medical procedures have been developed to help alleviate the pain and discomfort associated with spinal stenosis.

One method that has been developed to alleviate the pain and discomfort associated with spinal stenosis includes using an interspinous implant to distract the spinous processes of adjacent vertebra. The interspinous implant can be placed between the spinous processes to increase the distance between the spinous processes, while also allowing flexion, axial rotation and lateral bending. The use of an interspinous implant may, however, place an unnatural amount of stress on the spinous processes supporting the interspinous implant. This can be problematic, especially when the spinous process has been weakened by old age and/or another medical condition (such as by osteoporosis). Thus, if a spinous process is weak it may fracture or crack when using the implant. Accordingly, what is needed are surgical systems and methods which can increase the strength of a spinous process, thereby allowing a wide range of interspinous implants to be used to distract the spinous processes of adjacent vertebra.

BRIEF DESCRIPTION OF THE DRAWINGS

The accompanying drawings, which are incorporated into and constitute a part of this specification, illustrate one or more embodiments and, together with the detailed description, serve to explain the principles and implementations of the invention. In the drawings.

DETAILED DESCRIPTION

Embodiments are described herein in the context of systems and methods for injecting bone filler (e.g., bone cement) into the spine. Those of ordinary skill in the art will realize that the following detailed description is illustrative only and is not intended to be in any way limiting. Other embodiments of the present invention will readily suggest themselves to such skilled persons having the benefit of this disclosure. Reference will now be made in detail to implementations of embodiment of the present invention as illustrated in the accompanying drawings. The same reference indicators will be used throughout the drawings and the following detailed description to refer to the same or like parts.

One of the objects of the invention is to provide systems and methods to augment the strength of a spinous process to prevent it from fracturing or cracking when an interspinous implant is used to distract the spinous processes of adjacent vertebra. Another object of the invention is to generally strengthen weakened spinous processes and to repair cracked, fractured or otherwise damaged spinous processes. Another object of the invention is to provide a minimally invasive method of injecting bone filler into a spinous process. Other objects of the invention will become apparent from time to time throughout the specification and claims as hereinafter related.

Generally, a spinous process and/or lamina can by strengthened by injecting a bone-filler material, such as polymethylmethacrylate (PMMA—commonly known as bone cement), into the spinous process and/or lamina. To accomplish this task, a bone filler injection device having bone filler can be inserted directly into a spinous process and/or lamina. The bone filler injection device may include a spinal needle which can be used to penetrate the bone and deploy the bone filler. Once the bone filler injection device is placed at the desired location within the bone, the bone filler can be injected. After the desired amount of bone filler has been injected, the bone filler injection device can be removed from the bone as the bone filler is allowed to cure.

Figure 1:
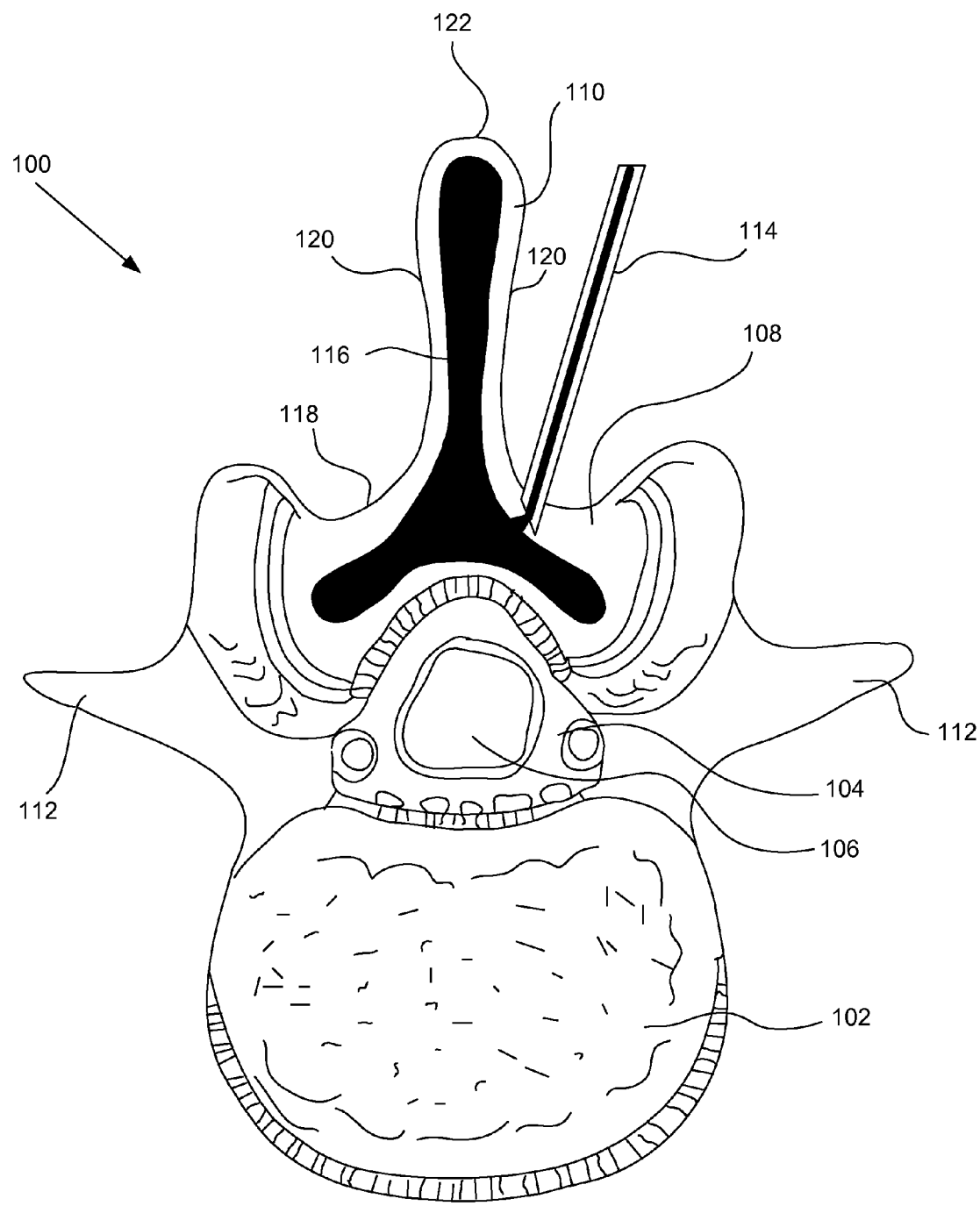
FIG. 1 illustrates a top cross-sectional view of a vertebra for an embodiment of the invention wherein a needle is inserted into the base of a spinous process.

Referring now to FIG. 1, a top cross-sectional view of a vertebra is illustrated. The vertebra, generally numbered 100, includes a vertebral foramen 104, a spinal canal 106 which is enclosed within the vertebral foramen 104, a lamina 108, a spinous process 110, and transverse processes 112. The spinous process 110 has a base 118, two sides 120 and an apex 122. In this embodiment, a spinal needle 114 which is incorporated within a bone filler injection device (not shown) is inserted at base 118 of the spinous process 110 near the junction of the spinous process 110 and lamina 108. The needle can be inserted to a depth which is superficial to the vertebral foramen 104 and spinal canal 106. Once the needle 114 is inserted, bone filler 116 can be injected into the lamina 108 and/or spinous process 110 through the needle 114. After the desired amount of bone filler 116 has been injected, the needle 114 can be removed as the bone filler 116 is allowed to cure.

Figure 2A:
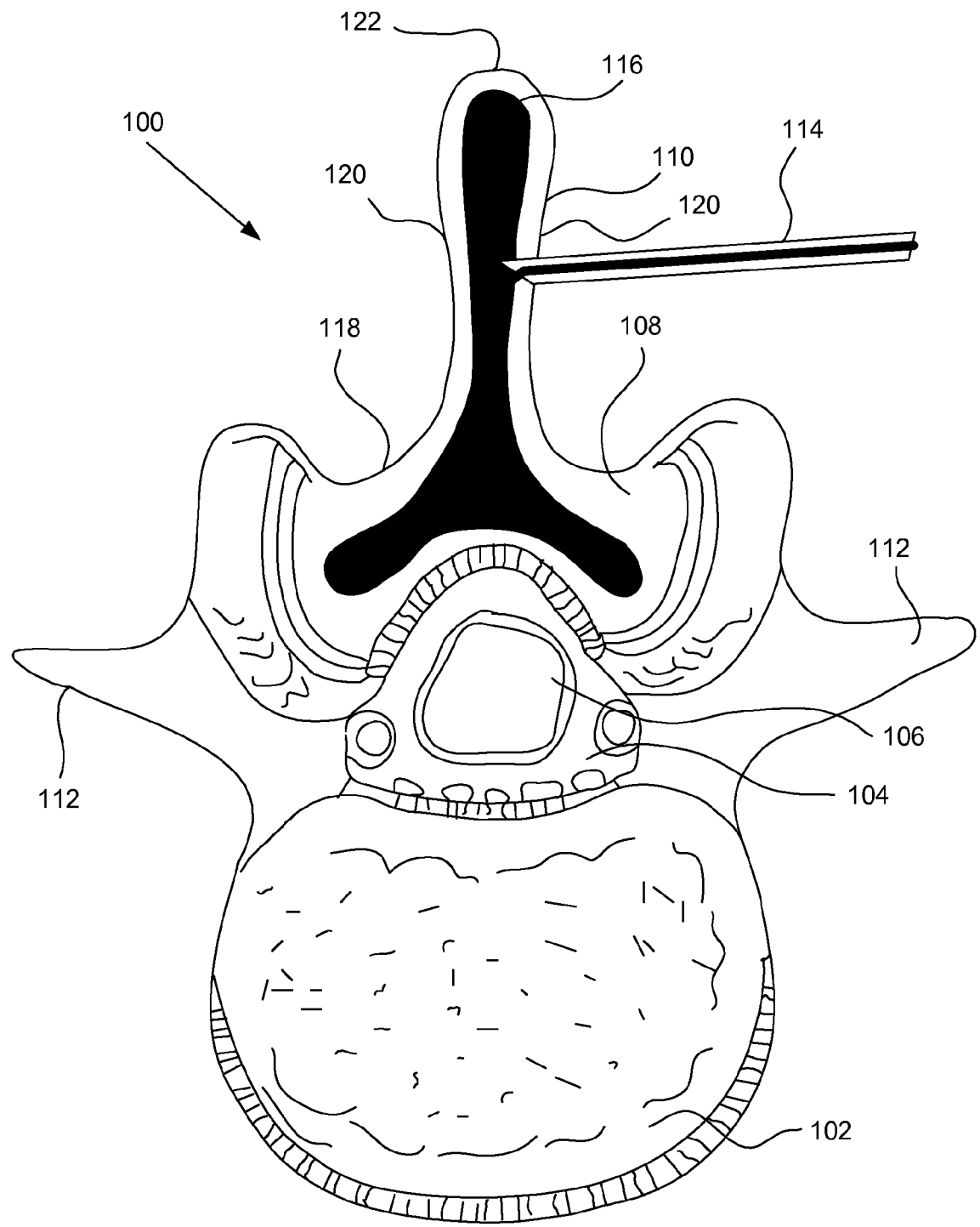
FIG. 2A illustrates a top cross-sectional view of a vertebra for an embodiment of the invention wherein a needle is inserted into the side of a spinous process.
Figure 2B:
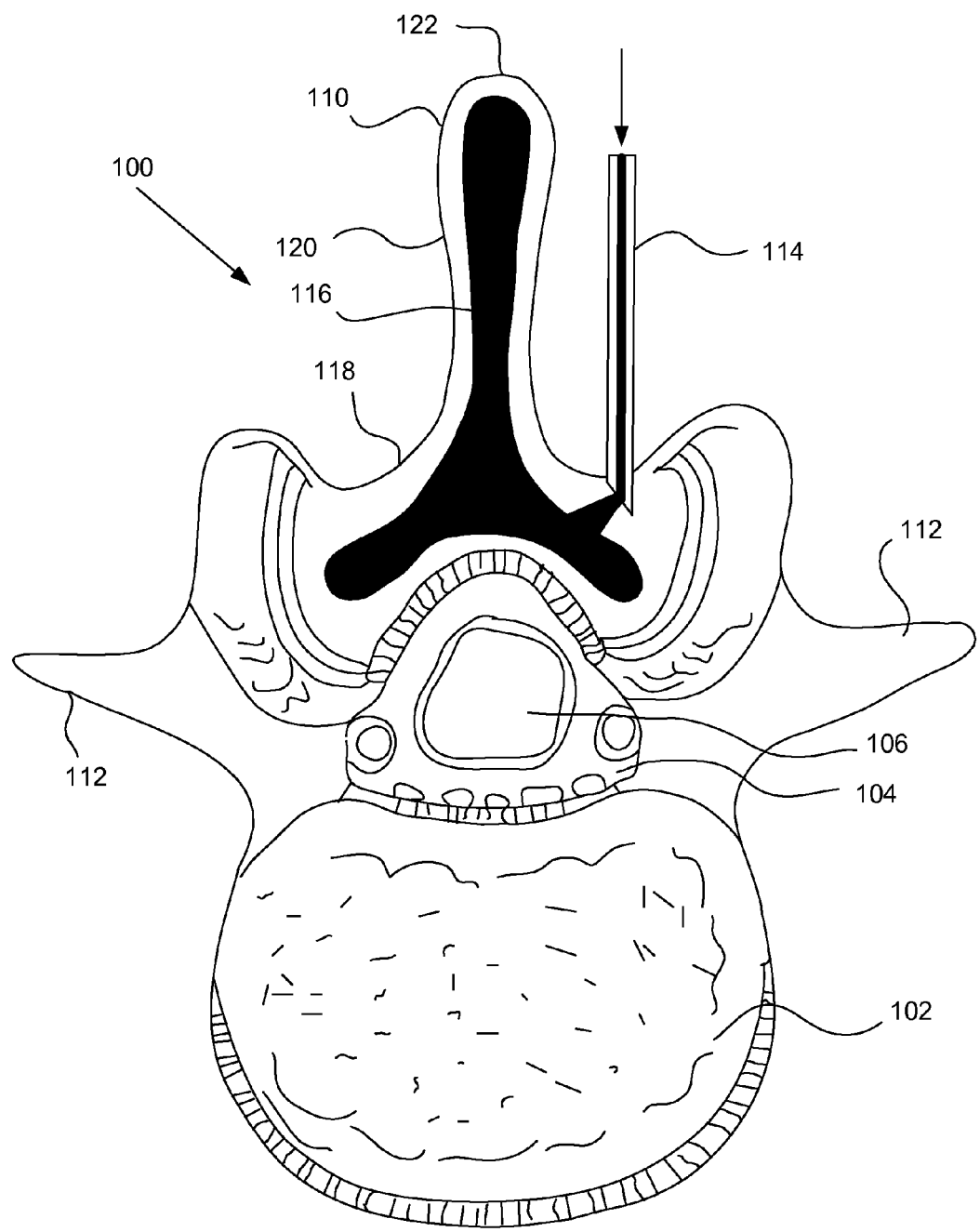
FIG. 2B illustrates a top cross-sectional view of a vertebra for an embodiment of the invention wherein a needle is inserted into a lamina.

FIGS. 2A-2B further illustrate different positions in which a spinal needle 114 can be inserted into the spinous process 110 and/or lamina 108 in accordance with embodiments of the present invention. As shown in FIG. 2A, the needle 114 can be transversely inserted into one side 120 of the spinous process 110 to a depth superficial to the other side 120 of the spinous process 110. In another embodiment, the spinal needle 114 can be inserted into the lamina 108 to a depth superficial to the vertebral foramen 104 and spinal canal 106 as shown in FIG. 2B. It is noted that the needle 114 can be inserted into the spinous process 110 and/or lamina 108 at any angle as envisioned by one having an ordinary skill in the art having the benefit of this disclosure.

Figure 3A:
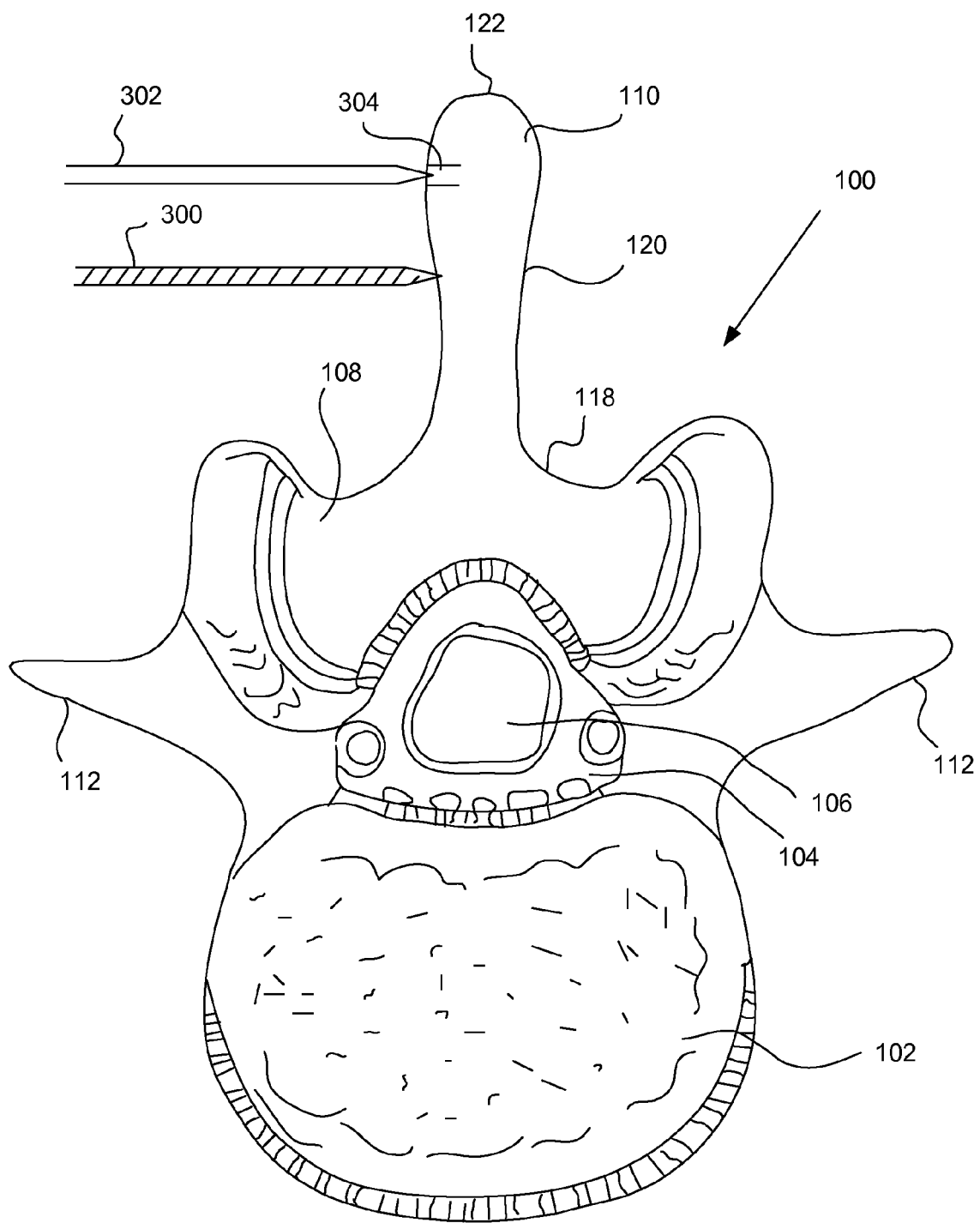
FIG. 3A illustrates a top cross-sectional view of a vertebra for an embodiment of the invention wherein a drill and a sharp point are inserted into the spinous process.
Figure 3B:
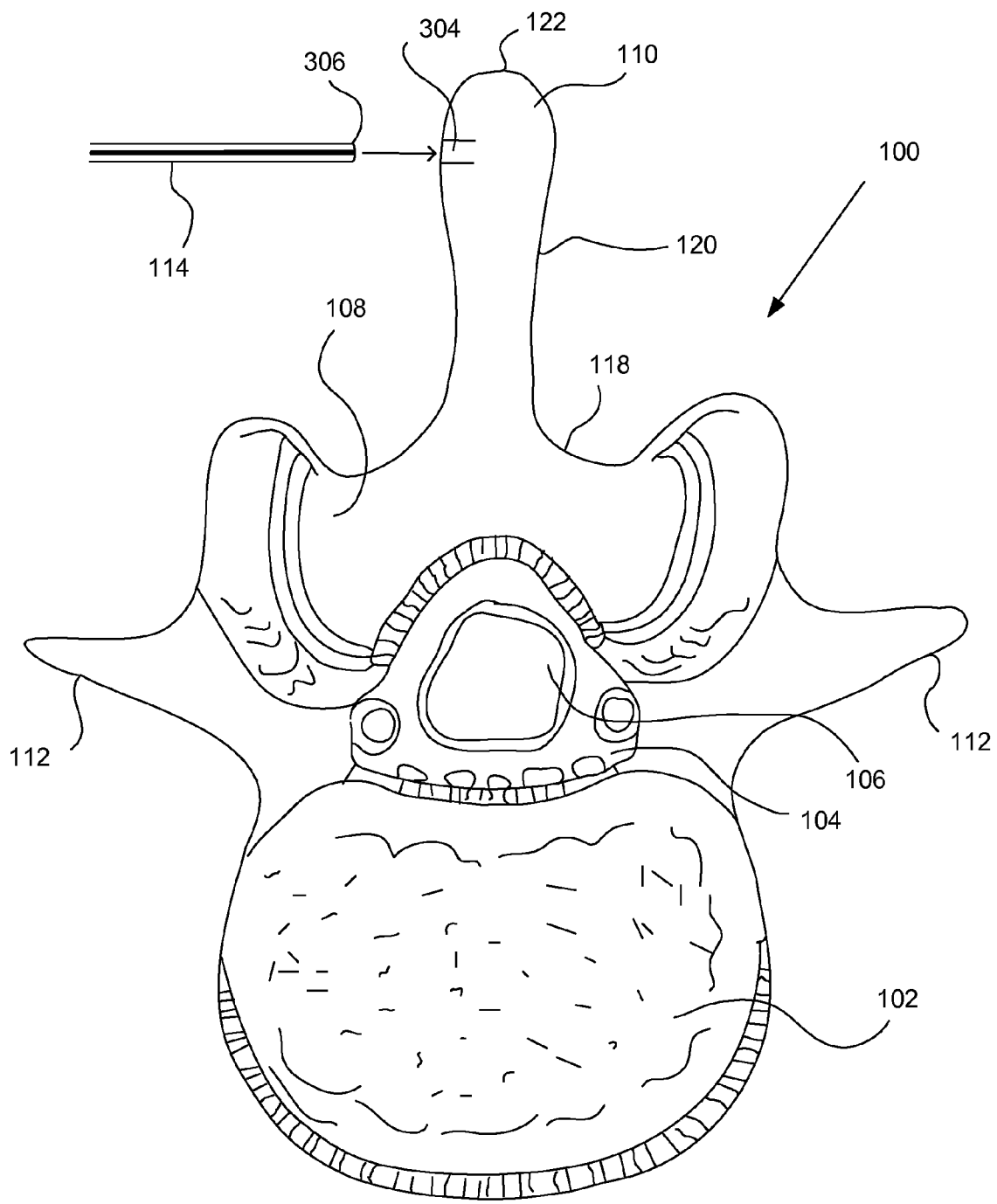
FIG. 3B illustrates a top cross-sectional view of a vertebra for an embodiment of the invention wherein a needle is inserted into the side of a spinous process.

The insertion of a spinal needle 114 into the spinous process 110 and/or lamina 108 may be accomplished using different techniques. In an embodiment, the spinal needle 114 includes a sharp tip which can be pushed and/or driven into the spinous process 110 and/or lamina 108. In another embodiment, a two-step technique may be used to introduce the bone filler 116 into the spinous process 110 and/or lamina 108. As shown in FIG. 3A, a sharp drill 300 and/or point 302 (e.g., an awl) can be used to enter the cortex of the spinous process 110 and/or lamina 108 to create an initial path 304 to the desired treatment site. Once a path 304 has been created, the sharp drill 300 and/or point 302 is removed and the needle 114 is inserted into the path 304 within the spinous process 110 and/or lamina 108 as shown in FIG. 3B. In an embodiment, the needle 114 may include a blunt tip 306 to prevent the needle 114 from extending past the endpoint of the path 304. This helps to ensure that the bone filler 116 remains inside the spinous process 110 and/or lamina 108. In an embodiment, diameter of the path 304 created by the sharp drill 300 and/or point 302 can be slightly smaller than the diameter of the needle 114 to prevent the filler 116 from flowing back out of the path 304 that was created. Accordingly, the path 304 should be narrow enough to require the surgeon to apply a force to the needle 116 in order to insert it into the path 304, but wide enough minimize the amount of force which is need to do so. Once inserted, the needle 116 should fit snugly within the path 304.

Turning now specifically to the spinal needle 114, the needle 114 can be any commercially available cannulated needle as envisioned by one having an ordinary skill in the art having the benefit of this disclosure. The needle 114 is preferably non-reactive, made of medical grade material and includes a stylet to prevent filler and/or bond blockage. The diameter of the needle 114 should be small enough to minimize injury to the body and yet large enough to permit the bone filler 116 to flow into the spinous process 110 and/or lamina 108. In an embodiment, an eleven to fourteen gauge needle can be used. It is, however, envisioned that smaller and/or larger needle diameters can also be used without deviating from the scope of the invention.

Figure 4A:
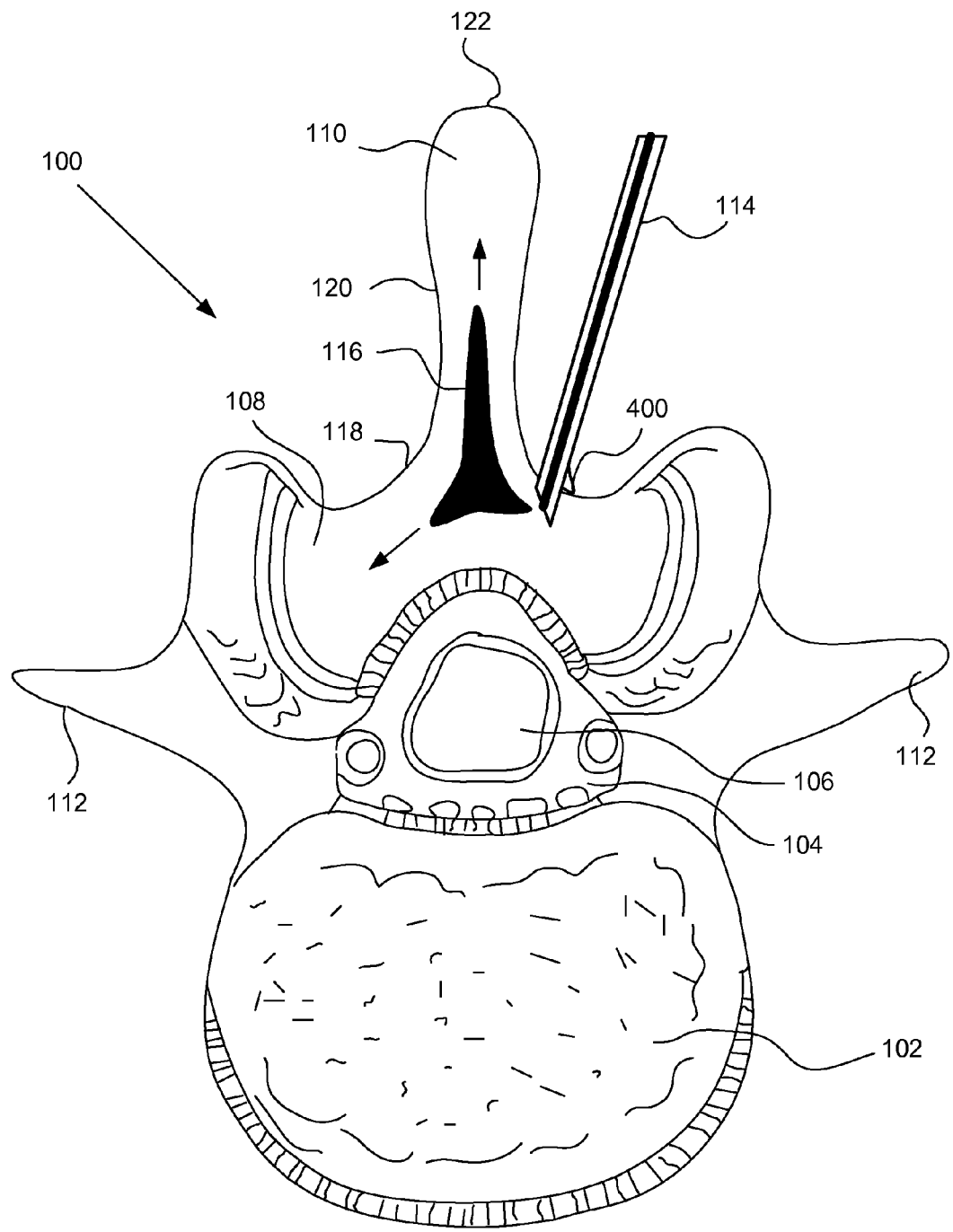
FIG. 4A illustrates a top cross-sectional view of a vertebra for an embodiment of the invention wherein a needle includes a stop.
Figure 4B:
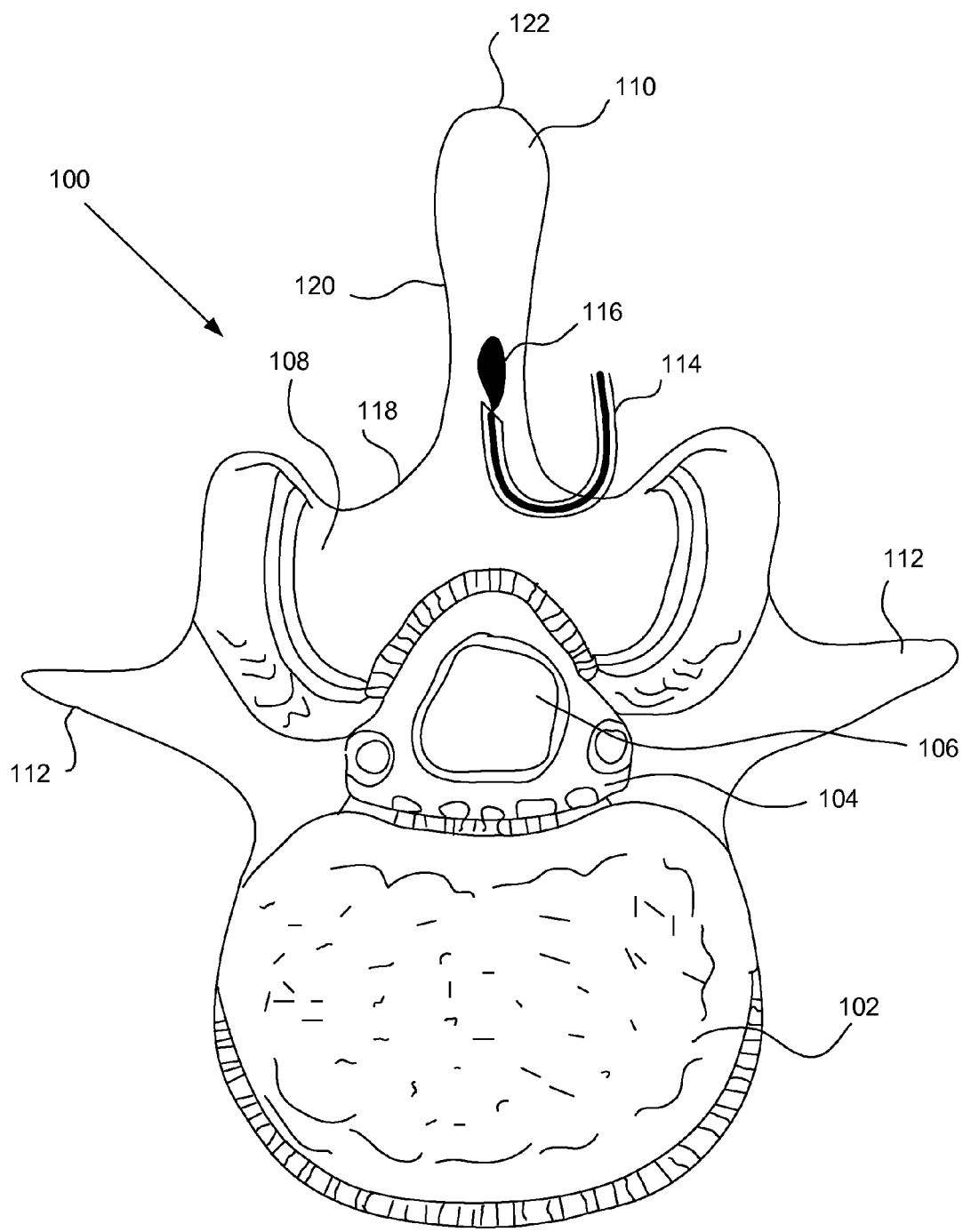
FIG. 4B illustrates a top cross-sectional view of a vertebra for an embodiment of the invention wherein a needle is curved.
Figure 4C:
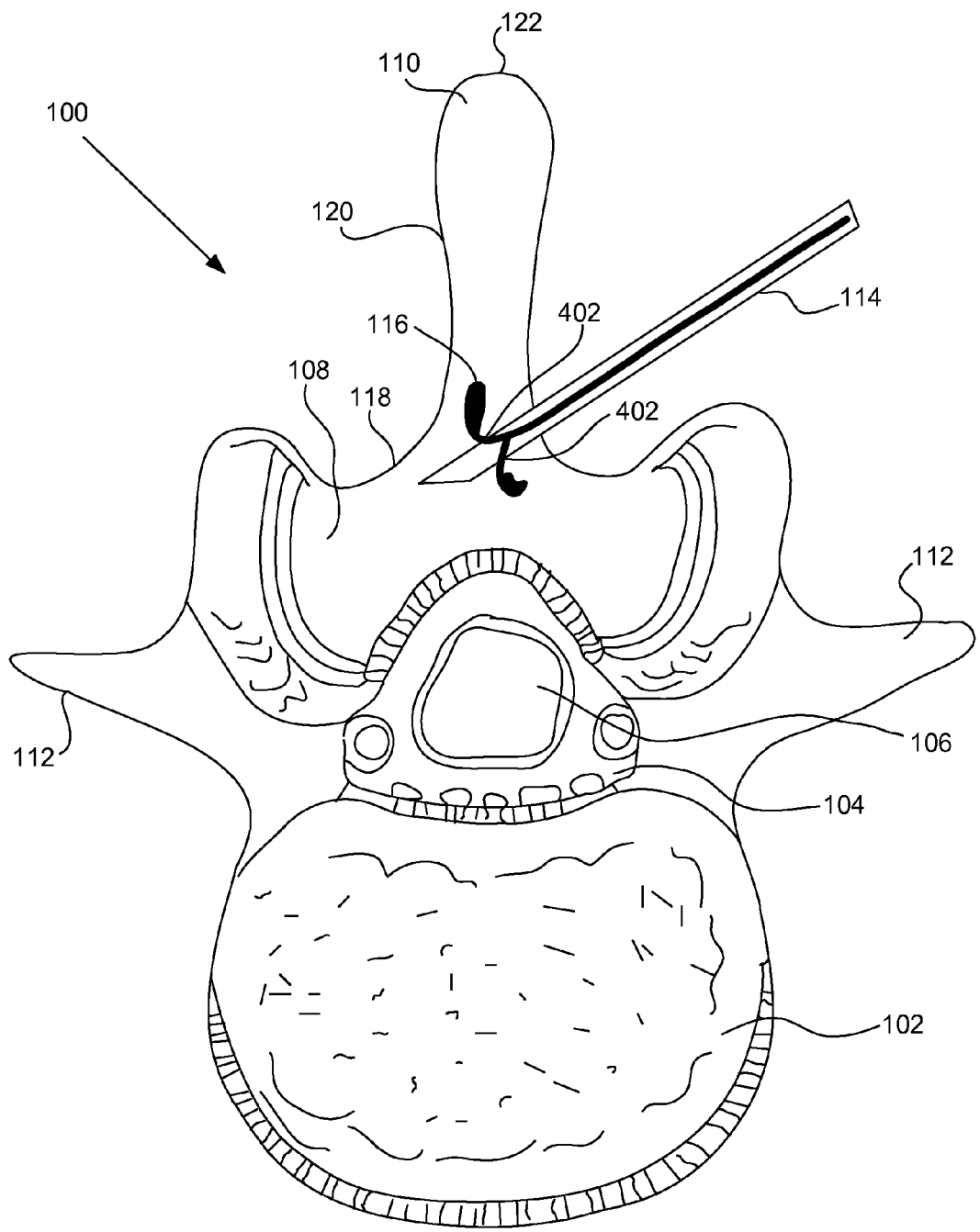
FIG. 4C illustrates a top cross-sectional view of a vertebra for an embodiment of the invention wherein a needle includes side outlets.
Figure 4D:
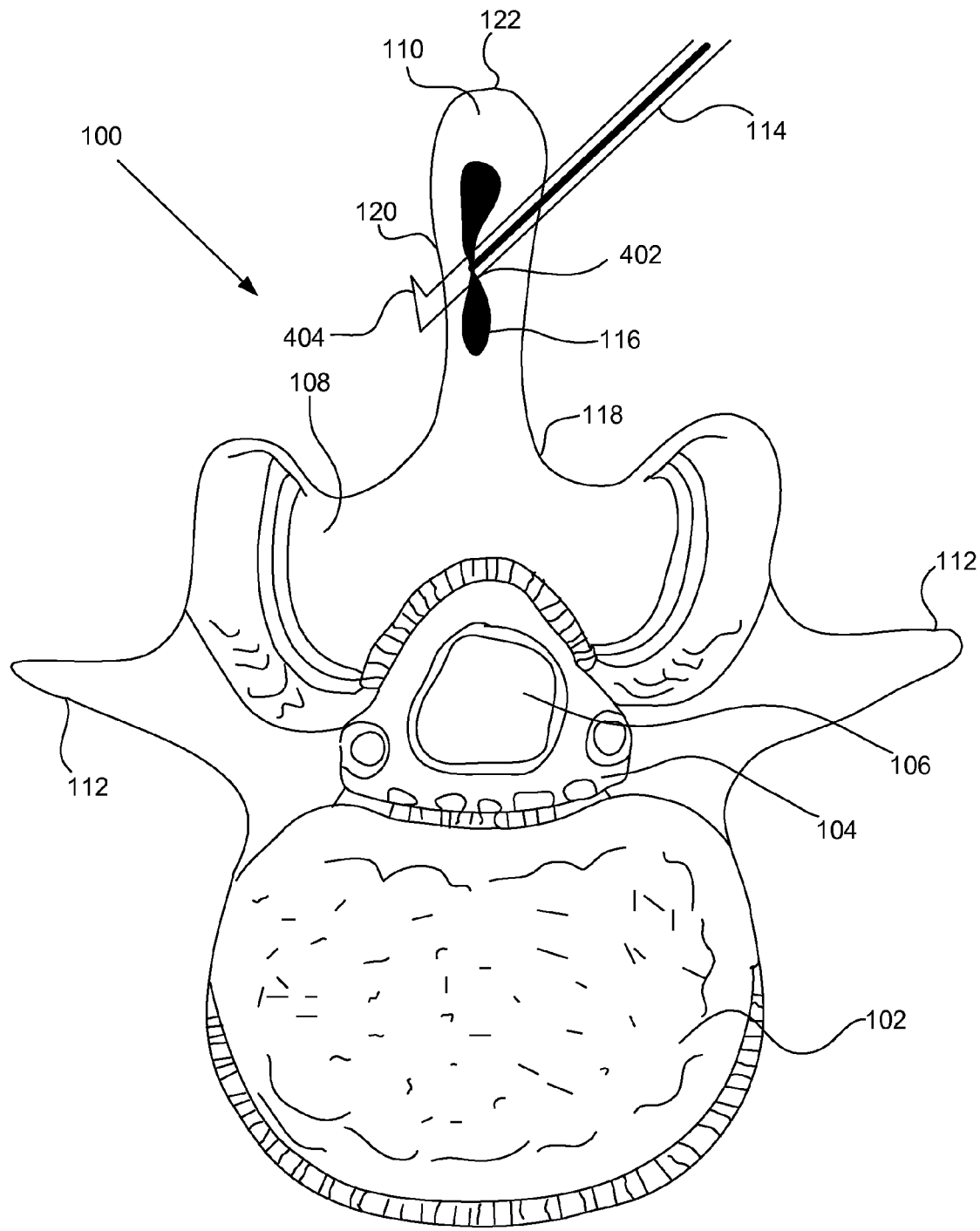
FIG. 4D illustrates a top cross-sectional view of a vertebra for an embodiment of the invention wherein a needle includes a hook.

Referring now to FIGS. 4A-4D, alternative embodiments of the spinal needle 114 are illustrated. FIG. 4A illustrates an embodiment of the needle 114 having a stop (or "bump") 400 that limits the depth of needle insertion. The stop 400 may be used to deliver the needle 114 to a specific desired treatment site. The stop 400 may also be used to ensure that the needle 114 is not inserted too deeply into the spinous process 110 and/or lamina 108. FIG. 4B illustrates an embodiment of the needle 114 having a curved configuration. The curved configuration of the needle 114 may allow the needle 114 to be inserted into a stronger portion of the spinous process 110 and/or lamina 108 and still reach as weaker and/or damaged portion of the spinous process 110 and/or lamina 108. FIG. 4C illustrates an embodiment of the needle 114 having side openings 402 for injection of the bone filler 116. FIG. 4D illustrates an embodiment of the needle 114 having side openings 402 as well as a hook 404 on the end of the needle 114 to hook back onto the spinous process 110 and/or lamina 108 once it is inserted. It is to be understood that the needle 114 may include any number and/or combination of the features set forth above as envisioned by one having an ordinary skill in the art having the benefit of this disclosure without deviating from the scope of the invention.

When inserting a spinal needle 114 into the base 118 or side 120 of a spinous process 110, devices to help guide the needle and/or provide support for the spinous process 110 during the surgical procedure may be desired and/or necessary. Accordingly, FIGS. 5 and 6A-6C illustrate different needle guide embodiments which can be used in conjunction with the spinal needle 114. In general, needle guides can assist in, among other things: directing the needle 114 to a specific point along the spinous process 110 and/or lamina 108, providing additional support to the spinous process 110 during the insertion process, and limiting the depth of the needle 114 during insertion.

Figure 5:
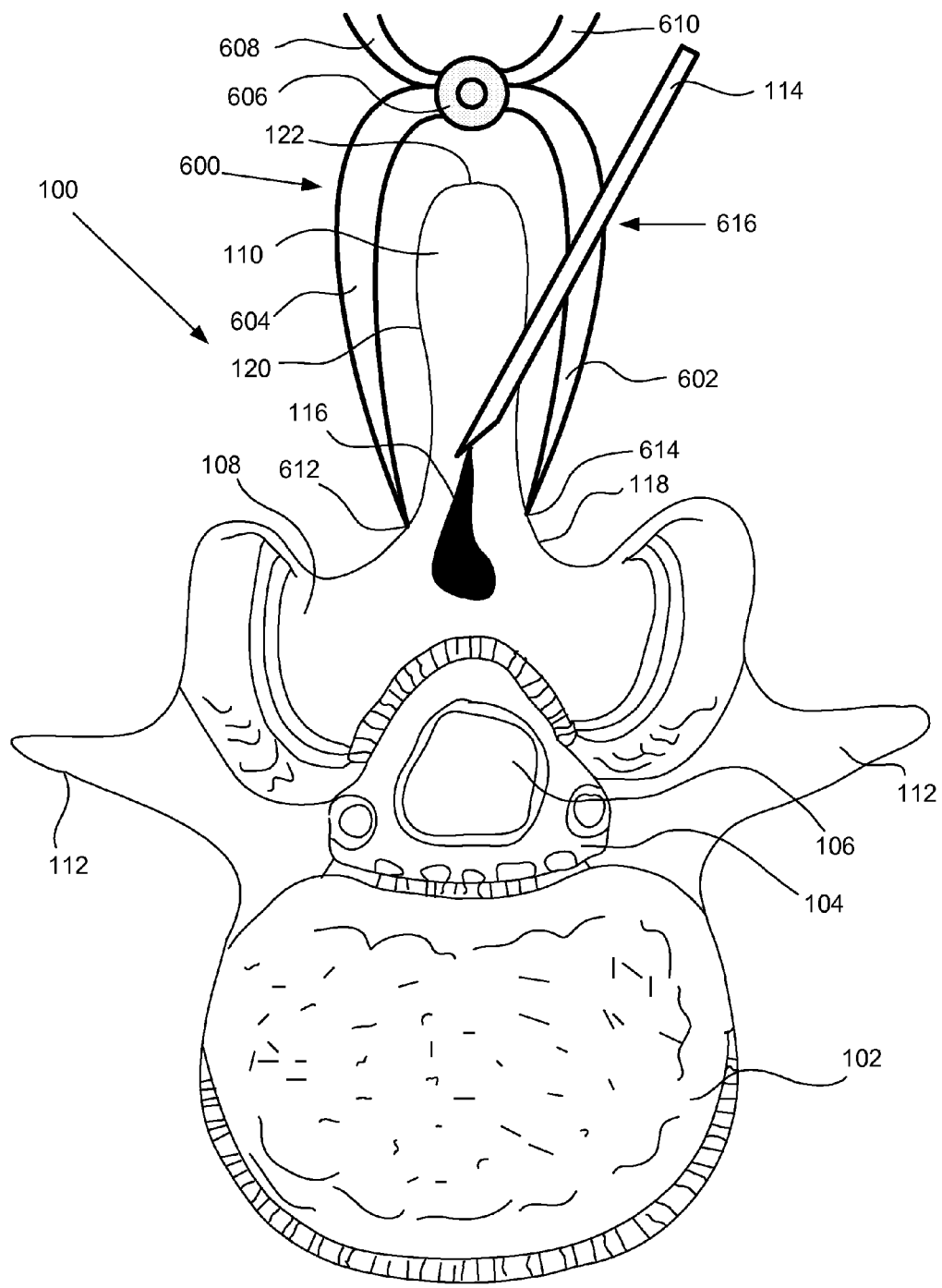
FIG. 5 illustrates a top cross-sectional view of a vertebra for an embodiment of the invention including a calliper guide element.

FIG. 5 illustrates an embodiment of a guide in accordance with the present invention. As shown in FIG. 5, guide 600 is a calliper which fits around a spinous process 110. The guide 600 includes two arms 602, 604, a joint 606, handles 608, 610, and two end points 612, 614. The two end points 612, 614 can grip the spinous process 110 as the handles are drawn closer together. Guide 600 can also include a needle guide aperture 616 through which a needle 114 can be inserted. Again the aperture 616 can help to support and direct the needle 114 during insertion as well as help to control the depth of needle insertion. The aperture 616 can be located at any point along the guide 600. FIG. 5 illustrates the guide 600 wherein the aperture 616 is located within and arm 602 of the guide 600. The guide can be made of a strong, non-reactive, medical grade material such as surgical stainless steel or titanium. In an embodiment, the ends 612, 614 of the guide 600 have sharp points which can be inserted into the spinous process 110 as the needle 114 is being inserted. The ends 612, 614 of the guide 600 may also be square shaped, rounded and/or include gripping elements in order to secure the guide 600 to the spinous process 110.

Figure 6A:
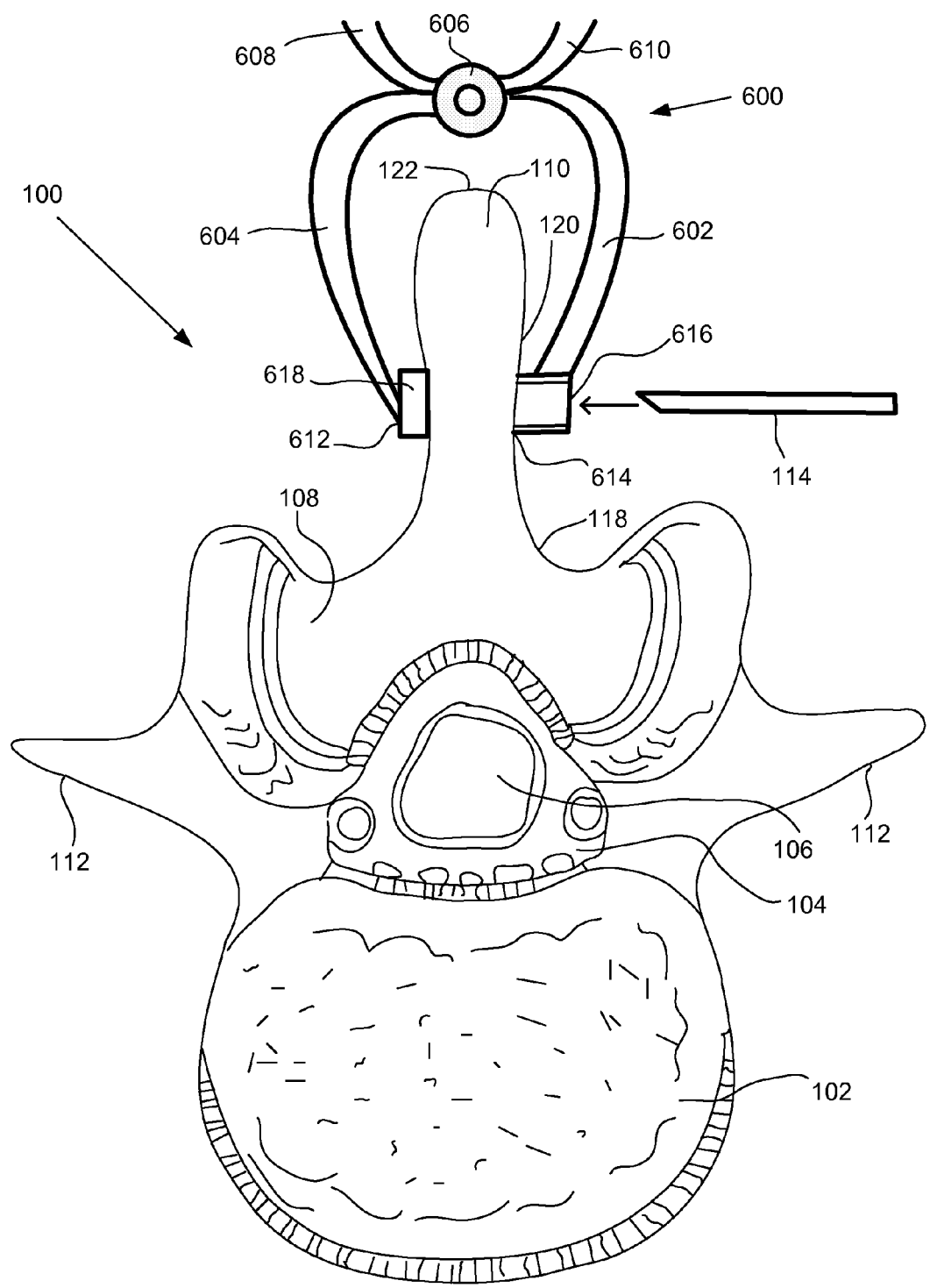
FIG. 6A illustrates a top cross-sectional view of a vertebra for an embodiment of the invention including a calliper guide element.

Referring now to FIG. 6A, another embodiment of the calliper guide 600 is illustrated. In this embodiment, the first end 612 of the guide includes a solid barrier 618 and the second end 614 of the guide includes an aperture 616. In this configuration, the needle 114 can be directed into the spinous process 110 transversely, thereby avoiding the possibility of entering the vertebral foramen 104 and/or the spinal canal 106. The barrier 618 can be used to prevent the needle 114 from extending past the other side of the spinous process 110, thereby ensuring that the bone filler 116 remains within the spinous process 110 and/or lamina 108.

Figure 6B:
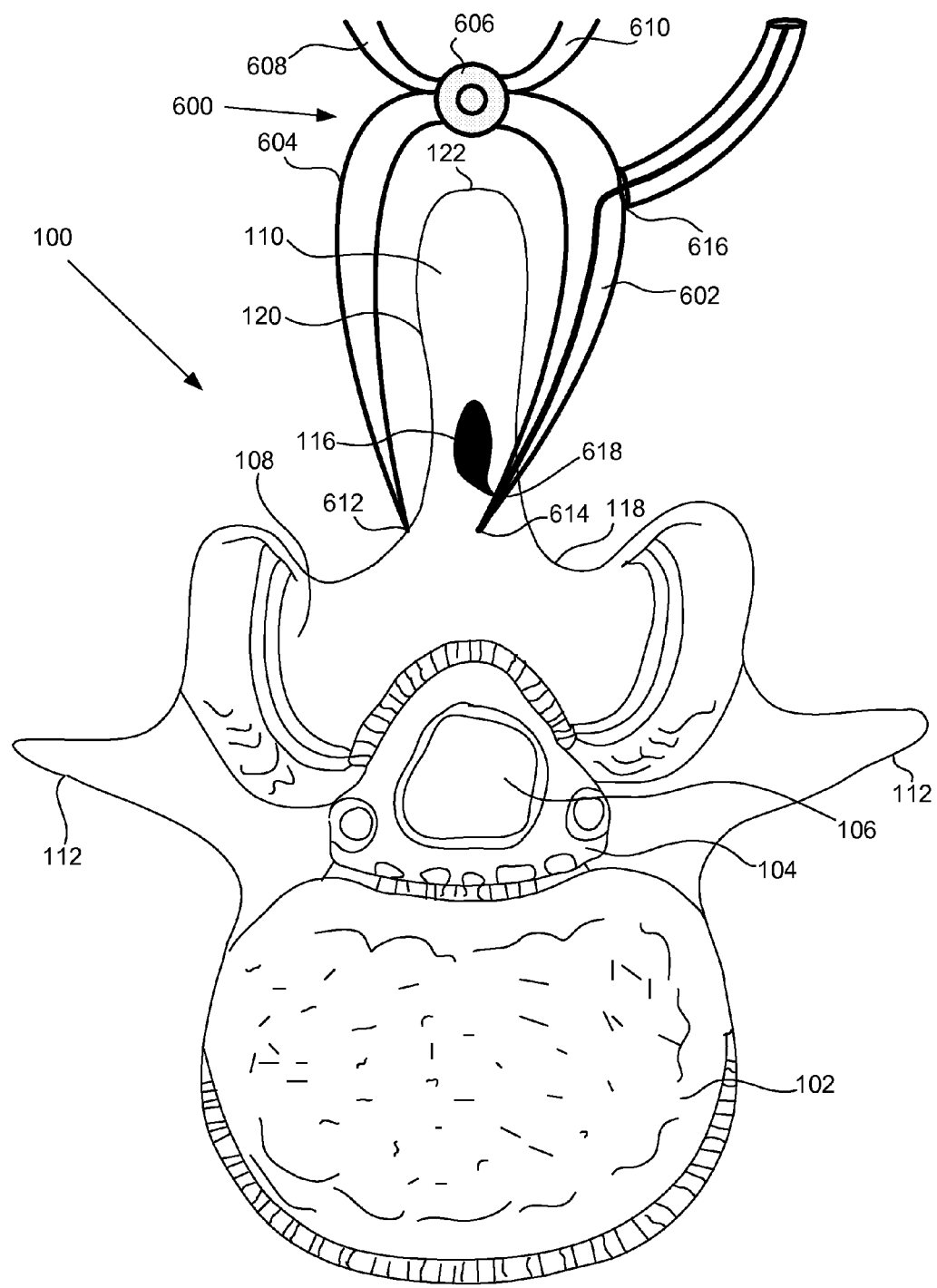
FIG. 6B illustrates a top cross-sectional view of a vertebra for an embodiment of the invention including a calliper guide element.

Referring now to FIG. 6B, another embodiment of the calliper guide 600 is illustrated. In this embodiment, the calliper guide 600 can itself be used insert the bone filler 116 into the spinous process 110. Thus, in this embodiment, the bone filler injection device would not include a spinal needle. As shown in FIG. 6B, the calliper guide 600 includes an end 614 and an arm 602 which is hollow. The hollow arm 602 includes two apertures, the first aperture 616 being located proximal to the joint 606 and the second aperture 618 being located proximal to the end 614 of the arm 602. Using this embodiment of the calliper guide 600, the end 614 which includes a sharp point can first be inserted into the spinous process 110. Once inserted, bone filler 116 can be injected into the first aperture 616 of the guide 600 and then inserted into the spinous process 110 through the second aperture 618.

Figure 6C:
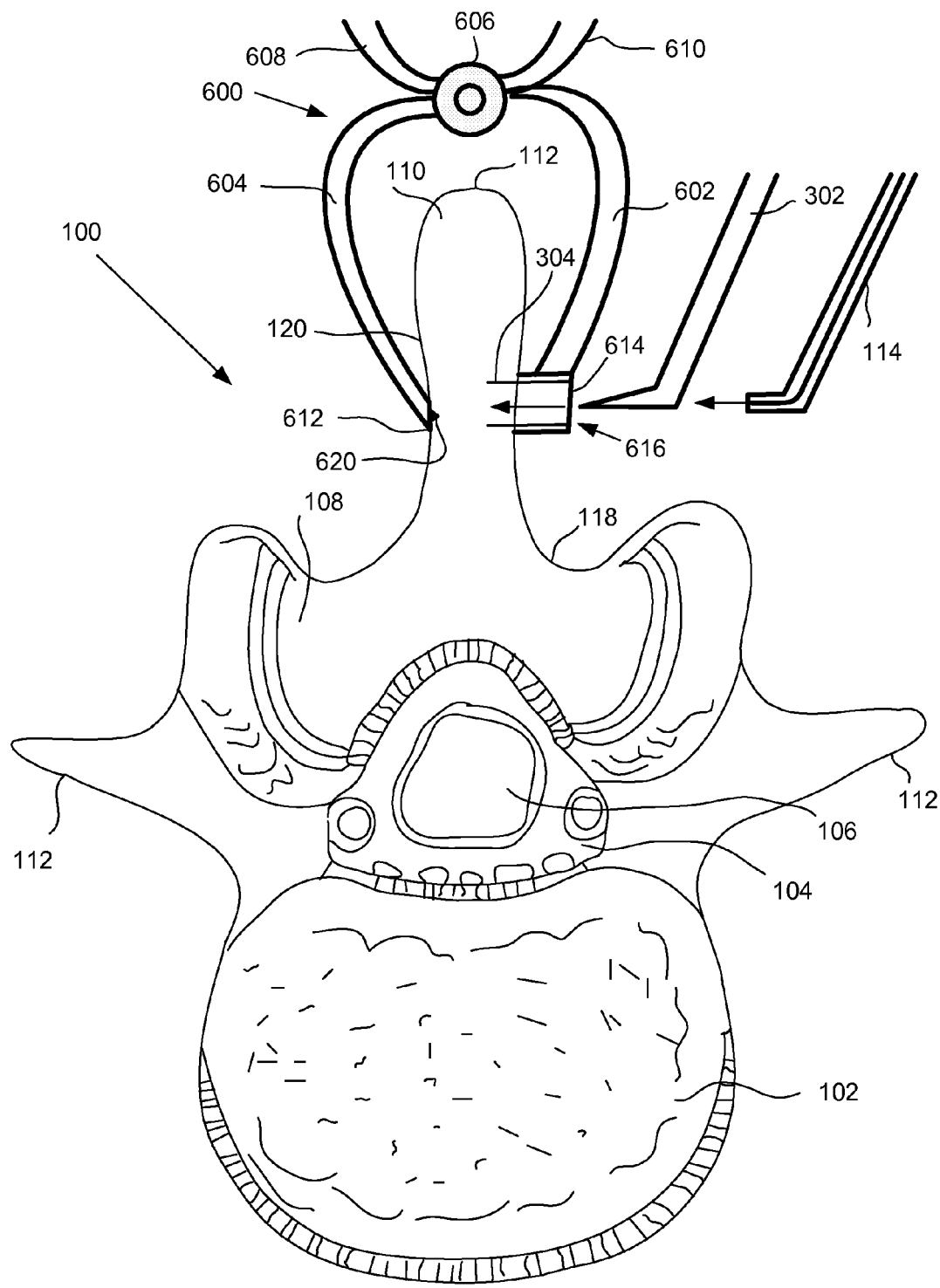
FIG. 6C illustrates a top cross-sectional view of a vertebra for an embodiment of the invention including a calliper guide element.

Referring now to FIG. 6C, another embodiment of a method for injecting bone filler into a spinous process using a calliper guide 600 is illustrated. As shown in FIG. 6C, the guide 600 includes a first end 612 and a second end 614. The first end 612 includes a gripping element 620 which secures the guide 600 to the spinous process 110. The second end 614 includes an aperture 616 through which a needle 114 can be inserted. In this embodiment, a sharp point 302 (such as an awl) can be inserted into the aperture 616 and used to enter the cortex of the spinous process 110 to create an initial path 304 to the desired treatment site. Once the path has been created, the sharp point 302 is removed and a needle 114 can be inserted into the path 304. In an embodiment, the sharp point 302 and/or the needle 114 can have an L-shape to facilitate the surgical process, whereby the sharp point 302 and needle 114 can be transversely directed into the spinous process 110 adjacent to the base 200 of the spinous process 110. The foregoing description of different needle guide embodiments is not intended to be exhaustive or limit the invention to the precise forms disclosed. Thus, various other needle guide supports can be used as envisioned by one having an ordinary skill in the art having the benefit of this disclosure without deviating from the scope of the invention.

Figure 7:
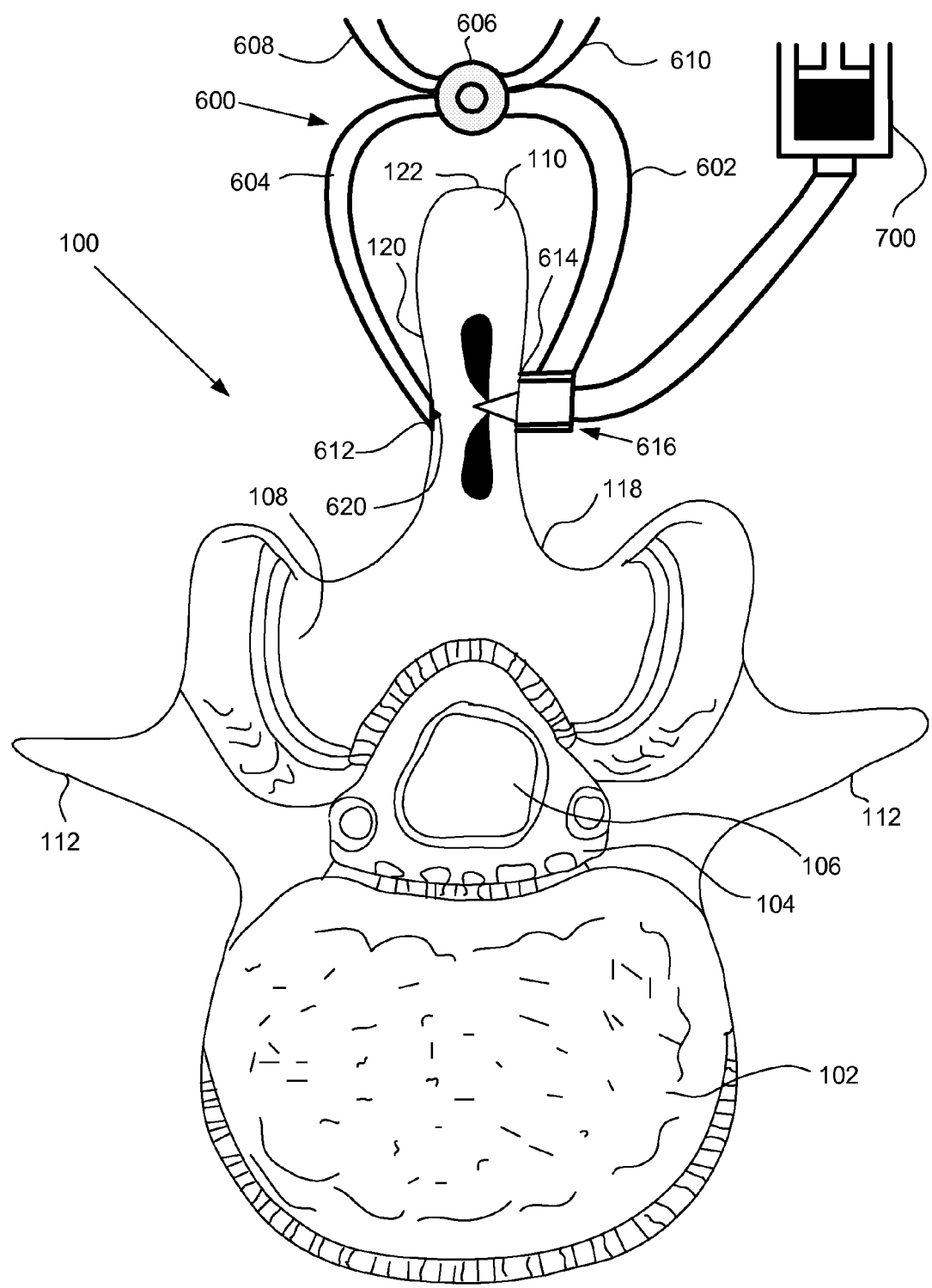
FIG. 7 illustrates a top cross-sectional view of a vertebra for an embodiment of the invention including a catheter.

The bone filler injection device described herein can include any commercially available device which is used to inject bone filler into a bone as envisioned by one having an ordinary skill in the art having the benefit of this disclosure. In an embodiment, the bone filler injection device includes a spinal needle 114 attached to a catheter 700 (as shown in FIG. 7). In another embodiment, the bone filler injection device includes a spinal needle 114, a flexible tube attached to the needle on one end, and a syringe attached to the flexible tube on the other end containing the bone filler. The surgical process used to inject the bone filler into the spine may also be monitored by the surgeon using any real-time imaging techniques, such as an x-ray fluoroscopy. Finally, the bone filler described above can include any appropriate commercially available bone filler as envisioned by one having an ordinary skill in the art having the benefit of this disclosure. In an embodiment, the bone filler can include polymethylmethacrylate (PMMA) or any other appropriate bone cement.

While embodiments and applications of this invention have been shown and described, it would be apparent to those skilled in the art having the benefit of this disclosure, that many more modifications than mentioned above are possible without departing from the inventive concepts herein.

The invention claimed is:

1. A method for strengthening a vertebra by injecting bone filler into the vertebra, comprising:
    inserting a spinal needle that is associated with a bone filler injection device into the vertebra, the bone filler injection device including bone filler, wherein the spinal needle is inserted into the vertebra through an entry point located at a base of a spinous process and on a lateral surface of the spinous process ventral of a posterior ridge of the spinous process and proximal to a junction between the spinous process and a lamina of the vertebra;
    injecting the bone filler into the vertebra;
    terminating the injection when a desired amount of bone filler has been injected into the vertebra;
    removing the bone filler injection device from the vertebra; and
    allowing the bone filler to cure within the vertebra.

2. The method of claim 1 further comprising the step of positioning the spinal needle within the vertebra at a desired location, wherein the desired location is superficial to the vertebral foramen and spinal canal.

3. The method of claim 1 further comprising the steps of using the spinal needle wherein the spinal needle has a longitudinal axis and wherein the longitudinal axis of the spinal needle is curved.

4. The method of claim 1 further comprising the steps of using the spinal needle with a stop that limits the depth of insertion.

5. The method of claim 1 further comprising the steps of using the spinal needle with a blunt tip.

6. The method of claim 1 wherein the spinal needle includes a plurality of side openings for injection of bone filler; and the injecting step including injecting the bone filler through the side openings.

7. The method of claim 1 further comprising the steps of using the spinal needle with a hook on the end of the needle.

8. A method for strengthening a vertebra by injecting bone filler into the vertebra, comprising:
    inserting a spinal needle that is associated with a bone filler injection device into the vertebra, the bone filler injection device including bone filler, wherein the spinal needle is inserted into the vertebra at a base of a spinous process proximal to the junction between the spinous process and a lamina of the vertebra;

injecting the bone filler into the vertebra;

terminating the injection when a desired amount of bone filler has been injected into the vertebra;

removing the bone filler injection device from the vertebra; and allowing the bone filler to cure within the vertebra; and using a guide device when inserting the spinal needle into the vertebra, wherein the guide device comprises a first arm having a first end point and a second arm having a second end point, wherein the first and second end points grip the spinous process during use.

9. The method of claim 8 wherein the guide device using step includes using the guide device which comprises a caliper.

10. The method of claim 8, wherein the guide device using step includes using the guide device wherein the first end point includes a solid barrier and the second end point includes an aperture for accepting the spinal needle.

11. The method of claim 8, wherein the guide device using step includes using the guide device wherein the first end point is used as the spinal needle, the first end point being inserted into the vertebra to inject the bone filler into the vertebra through the first end point.

12. A method for strengthening a vertebra by injecting bone filler into the vertebra, comprising:

positioning a guide device proximal to a spinous process of the vertebra, the guide device comprising a bore for accepting a spinal needle that is associated with a bone filler injection device, the bone filler injection device including bone filler;

inserting the spinal needle into the bore of the guide device;

inserting the spinal needle into the vertebra through an entry point located at a base of the spinous process on a lateral surface of the spinous process ventral of a posterior ridge of the spinous process and proximal to a junction between the spinous process and a lamina of the vertebra;

positioning the spinal needle within the vertebra at a desired location, wherein the desired location is superficial to the vertebral foramen and spinal canal;

injecting the bone filler into the vertebra;

terminating the injection when a desired amount of bone filler has been injected into the vertebra;

removing the bone filler injection device from the vertebra; and allowing the bone filler to cure within the vertebra.

13. A method for strengthening a vertebra by injecting bone filler into the vertebra, comprising:

inserting a spinal needle into the vertebra through an entry point located at a base of a spinous process and on a lateral surface of the spinous process ventral of a posterior ridge of the spinous process and proximal to the junction between the spinous process and a lamina of the vertebra;

injecting the bone filler into the vertebra through the needle;

terminating the injection when a desired amount of bone filler has been injected into the vertebra; and removing the needle from the vertebra.

14. A method for strengthening a vertebra by injecting bone filler into the vertebra, comprising:

inserting a spinal needle into the vertebra at a base of a spinous process proximal to the junction between the spinous process and a lamina of the vertebra;

injecting the bone filler into the vertebra through the needle;

terminating the injection when a desired amount of bone filler has been injected into the vertebra;

removing the needle from the vertebra; and using a guide device when inserting the spinal needle into the vertebra, wherein the guide device comprises a first arm having a first end point and a second arm having a second end point, wherein the first and second end points grip the spinous process during use.

15. The method of claim 14 wherein the guide device using step includes using the guide device which comprises a caliper.

16. The method of claim 14, wherein the guide device using step includes using the guide device wherein the first end point includes a solid barrier and the second end point includes an aperture for accepting the spinal needle.

* * * * *